United States Patent
Gibson et al.

(10) Patent No.: US 7,507,824 B2
(45) Date of Patent: Mar. 24, 2009

(54) SPIRO(2H-1BENZOPYRAN-2,4'-PIPERIDINE) DERIVATES AS GLYCINE TRANSPORT INHIBITORS

(75) Inventors: Samuel George Gibson, Motherwell (GB); David John Miller, Airdrie (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 10/637,681

(22) Filed: Aug. 8, 2003

(65) Prior Publication Data

US 2004/0029904 A1 Feb. 12, 2004

Related U.S. Application Data

(62) Division of application No. 10/130,557, filed as application No. PCT/EP00/11351 on Nov. 13, 2000, now Pat. No. 6,645,973.

(30) Foreign Application Priority Data

Nov. 17, 1999 (EP) .................. 99309137

(51) Int. Cl.
C07D 471/10 (2006.01)
A61K 31/438 (2006.01)

(52) U.S. Cl. ............... 546/15; 546/16; 546/18; 514/278

(58) Field of Classification Search .......... 546/15, 546/16; 514/278
See application file for complete search history.

(56) References Cited

U.S. PATENT DOCUMENTS 6,645,973 B1 * 11/2003 Gibson et al. ............ 514/278

FOREIGN PATENT DOCUMENTS

| EP | 0 518 805 | 12/1992 |
|---|---|---|
| EP | 951543 | 2/1998 |
| EP | 871440 | 3/2006 |
| WO | 93 25527 | 12/1993 |
| WO | 94 13678 | 6/1994 |
| WO | 94 18204 | 8/1994 |
| WO | 94 29317 | 12/1994 |
| WO | 95 22548 | 8/1995 |
| WO | 96 39386 | 12/1996 |
| WO | 97 37630 | 10/1997 |
| WO | WO 97/45115 | 12/1997 |
| WO | WO 97/45423 | 12/1997 |
| WO | WO 99/34790 | 7/1999 |
| WO | WO 00/07978 | 2/2000 |
| WO | 01 83476 | 11/2001 |

OTHER PUBLICATIONS

Bruekelmann et.al., "Protection of Primary Amines as N-Substituted 2,5-Dimethylpyrroles," *J. Chem. Soc. Perkin Trans. I* (1984) 2801-2807.
Javitt et al., "Glycyldodecylamide, a phencyclidine behavioral antagonist, blocks cortical glycine uptake: implications for schizophrenia and substance abuse," *Psychopharmacology 129* (1997) 96-98.
Kim et.al., "Cloning of the Human Glycine Transporter Type 1 : Molecular and Pharmacological Characterization of Novel Isoform Variants and Chromosomal Localization of the Gene in the Human and Mouse Genomes," *Molecular Pharm. 45* (1994) 608-617.
Morrow et.al., "Molecular cloning and functional expression of the human glycine transporter GlyT2 and chromosomal localisation of the gene in the human genome," *FEBS Letters 439* (1998) 334-340.
Sundberg et.al., "Cyclization of 2-[N-(Methylsulfonyl)anilino]acetaldehyde Diethyl Acetals to Indoles," *Journal of Organic Chemistry 49* (1984) 249-254.
Tsai et al., "Glycine transporter I inhibitor, N-Methylglycine (sarcosine), added to antipsychotics for the treatment of schizophrenia," *Biological Psychiatry 55* (2004) 452-456.
Wolfe et.al., "An Ammonia Equivalent for the Palladium-Catalyzed Amination of Aryl Halides and Triflates," *Tetrahedron Letters 38* (1997) 6367-6370.

* cited by examiner

Primary Examiner—Rita J Desai
(74) Attorney, Agent, or Firm—Susan Hess

(57) ABSTRACT

Formula I

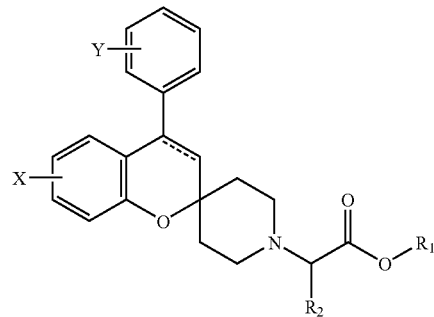

The present invention relates to spiro[2H-1-benzopyran-2,4'-piperidine] derivatives having general formula (I), or a pharmaceutically acceptable salt thereof. The invention also relates to pharmaceutical compositions comprising said derivatives, as well as to the use of these spiro[2H-1-benzopyran-2,4'-piperidine] derivatives in therapy, more specifically for the treatment of CNS disorders.

5 Claims, No Drawings

SPIRO(2H-1BENZOPYRAN-2,4'-PIPERIDINE) DERIVATES AS GLYCINE TRANSPORT INHIBITORS

This application is a Divisional Application of U.S. application Ser. No. 10/130,557, filed May 17, 2002, now U.S. Pat. No. 6,645,973, which is the 35 U.S.C. §371 filing of PCT/EP00/11351 filed Nov. 13, 2000.

The invention relates to spiro[2H-1-benzopyran-2,4'-piperidine] derivatives, to pharmaceutical compositions containing the same, as well as to the use of these spiro[2H-1-benzopyran-2,4'-piperidine] derivatives in therapy.

The simplest α-amino acid glycine has a number of important roles in the mammalian central nervous system (CNS). Along with γ-aminobutyric acid (GABA), it is a major post-synaptic inhibitory transmitter in the spinal cord and brainstem, acting through ligand gated ion channels. Interaction of glycine with these receptors can be antagonized by the alkaloid strychnine. These receptors are therefore referred to as 'strychnine sensitive' glycine receptors. Glycinergic neurotransmission is important in the processing and control of visual, auditory and motor signalling. Glycine is also an obligatory co-agonist along with glutamate at the N-methyl-D-aspartate (NMDA) receptor. Glycine therefore functions in excitatory transmission by modulating the actions of glutamate, the major excitatory neurotransmitter in the CNS. In addition the amino acid plays a role in the metabolism of peptides and proteins, including the exchange of one-carbon units.

Control of the availability of glycine for any of the above processes will potentially influence their function and provide means of treating a number of diseases and conditions. Apart from metabolism, one of the major processes controlling the concentrations of free glycine in the proximity of strychnine-sensitive and strychnine-insensitive glycine receptors is the functioning of selective high affinity glycine transporters. These proteins can actively limit the spread of glycine beyond the immediate environs of receptors, thus maintaining both spatial and temporal fidelity of receptor activation. Rapid sequestering of transmitter into neuronal or glial cells via the transporter will also conserve glycine for future release.

Glycine transporters have been cloned to reveal two major classes, GlyT-1 and GlyT-2. GlyT-1 is expressed throughout the brain with higher mRNA levels being detected in caudal areas and cellular localisation being predominantly glial.

Three isoforms of GlyT-1, 1a, 1b and 1c, arising from differential splicing and exon usage have been identified by Kim et al. (Molecular Pharm. 1994, 45, 608-617). The cloning and expression of a further human isoform GlyT-1d was recently disclosed in European Patent Application EP 951543 (Allelix Neuroscience, Inc.).

GlyT-2 distribution, as indicated by immunochemistry studies, corresponds closely to that of inhibitory 'strychnine sensitive' glycine receptors, particularly in the spinal cord.

By regulating the synaptic levels of glycine, the glycine transporters GlyT-1 and GlyT-2 are expected to selectively influence the activity at NMDA receptors and at strychnine-sensitive glycine receptors, respectively.

Compounds which alter the functional activity of glycine transporters may therefore result in changes in tissue glycine levels which can be useful in the treatment of a number of disease states. Such disease states include those associated with decreased or exaggerated function of NMDA receptors, namely psychosis, depression, dementia and other forms of impaired cognition, such as attention deficit disorders. NMDA receptors have further been implicated in conditions arising from neuronal cell death and neurodegeneration such as, for example, stroke (head trauma), Alzheimer's disease, Parkinson's disease and Huntington's disease. Enhanced inhibitory glycinergic transmission resulting from inhibition of GlyT-2 or GlyT-1 activity may be useful in the treatment of muscle hyperactivity associated with spasticity, myoclonus and epilepsy. Compounds elevating spinal glycine may also possess analgesic properties.

Compounds that inhibit glycine transport via the Gly-T1 or Gly-T2 transporters are disclosed in WO 97/45115 (TROPHIX PHARM. INC.), in WO 97/45423 (TROPHIX PHARM. INC.), in WO 99/34790 (ALLELIX NEUROSCIENCE INC.) and in WO 00/07978 (AKZO NOBEL N.V.) as compounds useful in the treatment of the neurological and neuropsychiatric disorders discussed above. There exists a need for additional compounds suitable for the treatment of psychiatric and neurological disorders, especially for compounds having a selective pharmacological profile.

It has now been found that spiro[2H-1-benzopyran-2,4'-piperidine] derivatives having the general formula I

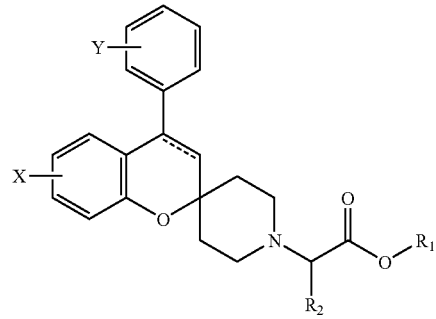

Formula I wherein
the dotted line represents an optional bond;
Y represents 1-4 substituents independently selected from hydrogen, halogen, $(C_{1-6})$alkyl (optionally substituted with one or more halogens), $(C_{1-6})$alkyloxy (optionally substitued with one or more halogens or with $(C_{3-6})$cycloalkyl), $(C_{2-6})$alkenyloxy, $(C_{2-6})$alkynyloxy, $(C_{3-6})$cycloalkyloxy, $(C_{6-12})$aryloxy, $(C_{7-15})$arylalkyloxy, heteroaryloxy, heteroarylalkyloxy, $SR_3$, $NR_3R_4$, $OSO_2R_5$ and $NR_3SO_2R_4$;
2 substituents Y may together form O—$(CH_2)$n-O or O—$(CF_2)$n-O, where n is 1 or 2; or Y represents a fused $(C_{5-6})$aryl group;
X represents 1-3 substituents independently selected from hydrogen, halogen, hydroxy, $(C_{1-4})$alkyloxy, $SR_3$, $NR_3SO_2R_4$ and $(C_{1-4})$alkyl, optionally substituted with halogen;
$R_1$ is hydrogen, $(C_{1-4})$alkyl or $(C_{6-12})$aryl;
$R_2$, $R_3$ and $R_4$ are independently hydrogen or $(C_{1-4})$alkyl;
$R_5$ is $(C_{1-4})$alkyl (optionally substituted with one or more halogens) or $(C_{6-12})$aryl (optionally substituted with $(C_{1-4})$ alkyl);
or a pharmaceutically acceptable salt thereof, selectively inhibit glycine transport by the human GlyT-1 transporter as compared to the human GlyT-2 transporter, and can be used in the treatment or prevention of schizophrenia, depression, dementia and other forms of impaired cognition, or of neurodegenerative diseases like Alzheimer's, Parkinson's and Huntington's disease, or of muscle hyperactivity associated with spasticity, myoclonus and epilepsy.

The term ($C_{1-6}$)alkyl, as used in the definition of formula I, means a branched or straight chain alkyl group having 1-6 carbon atoms, like hexyl, pentyl, neopentyl (2,2-dimethylpropyl), butyl, isobutyl, tertiary butyl, propyl, isopropyl, ethyl and methyl. Likewise, the term ($C_{1-4}$)alkyl refers to an alkyl group having 1-4 carbon atoms.

In the term ($C_{1-6}$)alkyloxy, ($C_{1-6}$)alkyl means a branched or an unbranched alkyl group as previously defined. The ($C_{1-6}$)alkyloxy group may be substituted with 1-3 halogens or with ($C_{3-6}$)cycloalkyl, which means a cyclic alkyl group having 3-6 carbon atoms, like cyclopropyl, cyclobutyl, cyclopentyl or cyclohexyl. Examples of such substituted ($C_{1-6}$)alkyloxy groups are trifluoromethyloxy and cyclopropylmethyloxy.

The term halogen means F, Cl, Br, or I. When halogen is a substituent at an alkyl group, F is preferred. A preferred halogen substituted alkyl group is trifluoromethyl.

The term ($C_{2-6}$)alkenyl, such as used in the term ($C_{2-6}$)alkenyloxy, means a branched or straight chain alkenyl group having 2-6 carbon atoms, such as ethenyl (vinyl), 2-propenyl (allyl), isopropenyl and 2-butenyl.

The term ($C_{2-6}$)alkynyl, such as used in the term ($C_{2-6}$)alkynyloxy, means a branched or straight chain alkynyl group having 2-6 carbon atoms, such as propargyl.

In the term ($C_{6-12}$)aryloxy, as used in the definition of formula I, ($C_{6-12}$)aryl means an aromatic hydrocarbon group having 6-12 carbon atoms, such as phenyl, naphthyl, tetrahydronaphthyl, indenyl or biphenyl. These aromatic groups may be substituted with halogen, or with ($C_{1-4}$)alkyl or ($C_{1-4}$)alkyloxy, wherein ($C_{1-4}$)alkyl has the previously given meaning and may be substituted with halogenror ($C_{1-4}$)alkyloxy.

The term ($C_{7-15}$)arylalkyl, as used in the definition of Formula I, means an arylalkyl group having 7 to 15 carbon atoms, wherein the alkyl group is a ($C_{1-6}$)alkyl group and the aryl group is a ($C_{6-12}$)aryl as previously defined. Phenyl($C_{1-6}$)alkyl groups are preferred arylalkyl groups, such as benzyl.

The term heteroaryl, such as used in the term heteroaryloxy, means a substituted or unsubstituted aromatic group having 6-12 carbon atoms, including at least one heteroatom selected from N, O and S, like for example imidazolyl, thienyl, benzthienyl, quinolinyl and indolyl. The heteroaryl group may carry substituents as listed for the aryl group.

Heteroarylalkyl groups are analogs of the (7-15)arylalkyl groups, including at least one heteroatom selected from N, O and S.

In the definition of formula I, Y can represent a fused ($C_{5-6}$)aryl group, which means that Y is a 5 or 6-membered aromatic ring fused to the benzene ring to which X is attached to form a ($C_{11-12}$)aromatic ring system, like a naphthalene or an indene ring.

In addition to the definition of $R_1$, the O-$R_1$ group in Formula I may be any other group from which the free acid ($R_1$ is hydrogen) can be generated (in vivo). Such alternative acid precursors or prodrugs, such as further ester or amide derivatives, are known in the art, and are within the scope of the present invention.

The spiro[2H-1-benzopyran-2,4'-piperidine] derivatives of formula I and their salts may contain one or more stereogenic centres and may exist therefore as stereoisomers. The present invention includes these stereoisomers within its scope, as well as enantiomers of the compounds of formula I and their salts, substantially free, i.e. associated with less than 5%, preferably less than 2%, in particular less than 1% of the other enantiomer, and mixtures of such stereoisomers in any proportions including the racemic mixtures containing substantially equal amounts of the two enantiomers.

Preferred are the spiro[2H-1-benzopyran-2,4'-piperidine] derivatives of formula I wherein the dotted line represents a bond, while those compounds wherein in addition $R_1$ and $R_2$ are both hydrogen are more preferred.

Especially preferred spiro[2H-1-benzopyran-2,4'-piperidine] derivatives of the invention; and of salts thereof, correspond to compounds of formula I wherein the dotted line is a bond, $R_1$ and $R_2$ are hydrogen, and wherein Y represent a para-substituent selected from chloro, bromo, ($C_{1-4}$)alkyloxy, ($C_{1-4}$)alkenyloxy, ($C_{1-4}$)-alkynyloxy and $NR_3R_4$, and 1 or 2 meta-substituents selected among the halogens, the preferred selection being fluoro. Specific examples of preferred substitution patterns Y are: 3-fluoro-4-methyl; 3-fluoro-4-chloro; 3-fluoro-4-dimethylamino and 3,5-difluoro-4-dimethylamino. Especially preferred are compounds according to formula I wherein Y represents 3-fluoro-4-alkyloxy, in particular 3-fluoro-4-n-propoxy and 3-fluoro-4-n-butoxy, and 3,5-difluoro-4-alkyloxy.

Spiro[2H-1-benzopyran-2,4'-piperidine] derivatives of general formula I may be prepared using a sequence of reactions in which 2'-hydroxyacetophenone derivatives of Formula II, wherein X has the meanings as previously defined, are utilized as starting materials which are readily available either commercially or using synthesis methods known to the person skilled in the art of synthetic organic chemistry. The 2'-hydroxyacetophenone derivatives II are condensed with 1-methyl-4-piperidone [R is methyl; as an alternative 1-benzyl-4-piperidone (R is benzyl) may be used, the benzyl group being often more easily removed than the methyl group (see Scheme C)] in methanol solution in the presence of pyrrolidine to provide N-methyl-spiro[2H-1-benzopyran-2,4'-piperidine]-4(3H)-one derivatives having Formula III as shown in Scheme A.

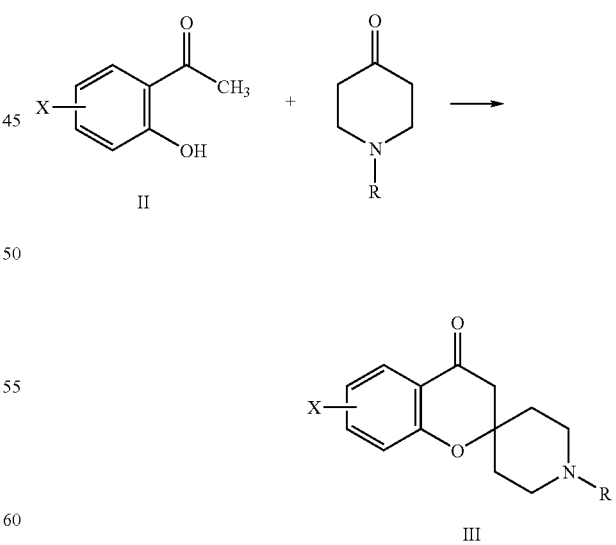

The spiro-keto derivatives of Formula III are subsequently treated, as shown in Scheme B, with a Grignard reagent having formula IV, wherein Y has the meaning as previously defined, in a suitable solvent, like tetrahydrofuran, to give the 4-aryl-N-methyl- or N-benzyl-spiro[2H-1-benzopyran-2,4'-piperidine] derivatives of formula V after treatment with acid.

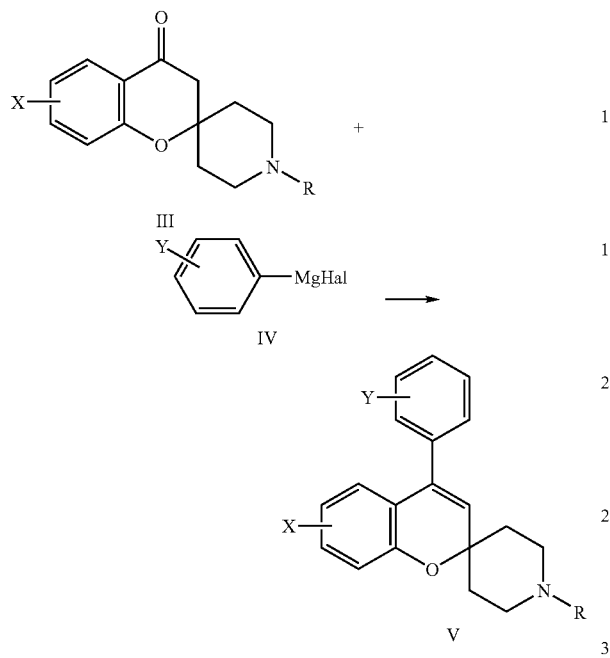

Alternatively, compounds according to Formula V can be prepared by conversion of a spiro-keto derivative of Formula III, wherein R is H, methyl or benzyl, to the enoltriflate derivative III", and subsequent Suzuki coupling reaction with a phenylboronic acid derivative IV" (Scheme B").

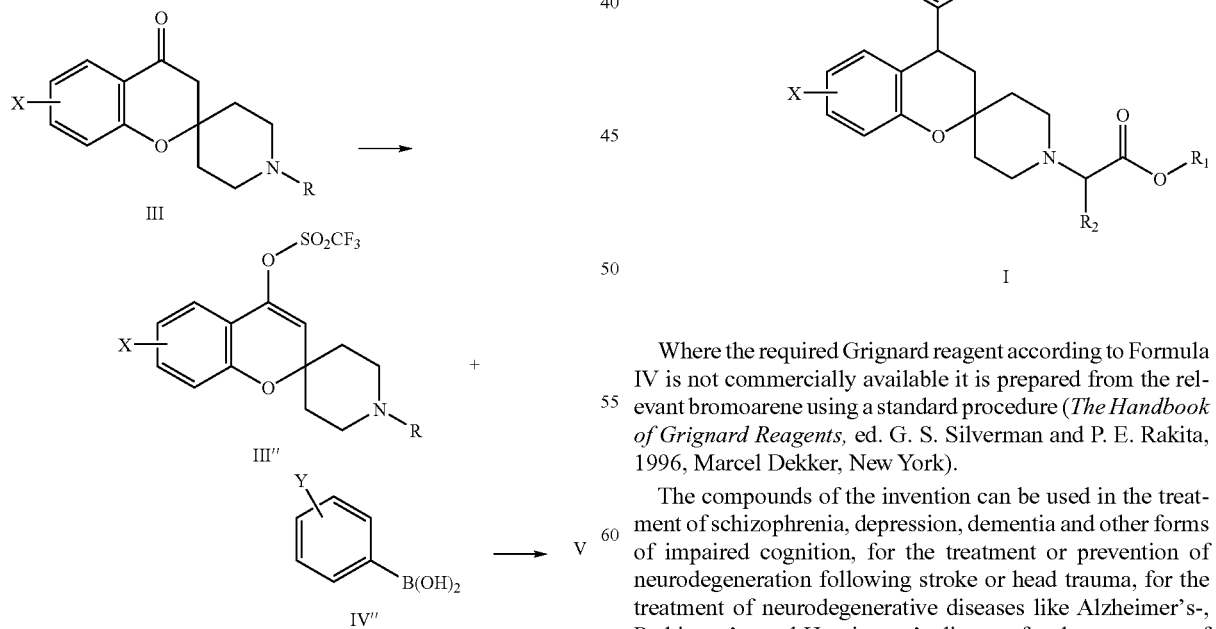

N-Dealkylation of the compounds according to formula V using 1-chloroethyl chloroformate in a chlorinated solvent such as 1,3-dichloropropane or dichloromethane yields the intermediate 4-aryl-spiro[2H-1-benzopyran-2,4'-piperidine] derivatives of Formula VI, which are subsequently alkylated on reaction with $HalCH_2R_2\text{-}COOR_1$, wherein $R_1$ may be $(C_{1-4})$alkyl or $(C_{6-12})$aryl and $R_2$ has the meaning as previously defined and Hal means halogen, preferably bromo, to give the 4-aryl-spiro[2H-1-benzopyran-2,4'-piperidine] derivatives of Formula I, as shown in Scheme C, the ester function of which may be hydrolysed to the compounds of formula I wherein $R_1$ is hydrogen.

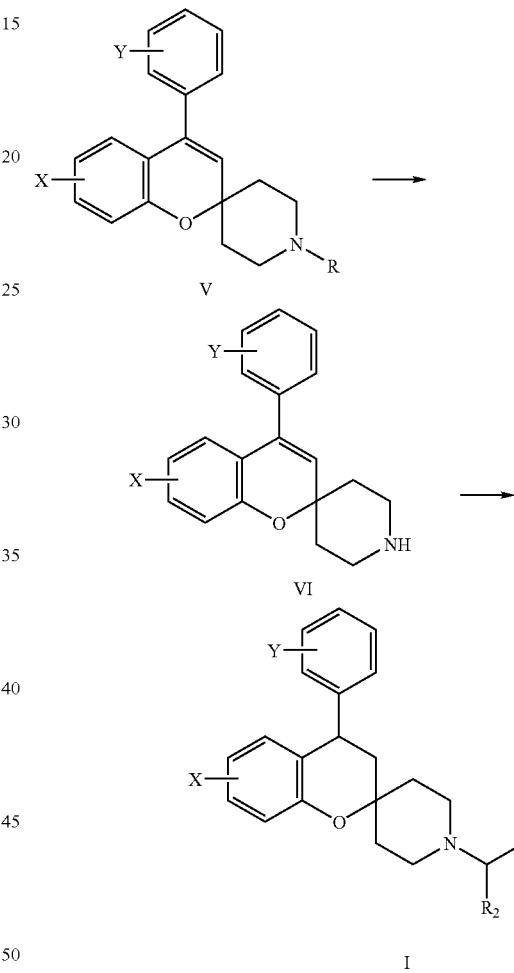

Where the required Grignard reagent according to Formula IV is not commercially available it is prepared from the relevant bromoarene using a standard procedure (*The Handbook of Grignard Reagents,* ed. G. S. Silverman and P. E. Rakita, 1996, Marcel Dekker, New York).

The compounds of the invention can be used in the treatment of schizophrenia, depression, dementia and other forms of impaired cognition, for the treatment or prevention of neurodegeneration following stroke or head trauma, for the treatment of neurodegenerative diseases like Alzheimer's-, Parkinson's- and Huntington's disease, for the treatment of muscle hyperactivity associated with spasticity, myoclonus and epilepsy, for the treatment or prevention of pain, mood disorders or learning disorders.

The compounds of this invention may possess one or more stereogenic centres and can therefore be obtained as pure stereoisomers, or as a mixture of stereoisomers. Methods for asymmetric synthesis whereby the pure stereoisomers are obtained are well known in the art, e.g. synthesis with chiral induction, enantioselective enzymatic ester hydrolysis, crystallization of salts which are obtained from optically active acids and the racemic mixture, separation of stereoisomers or enantiomers using chromatography on chiral media, or on straight phase or reversed phase chromatography media. Such methods are for example described in *Chirality in Industry* (edited by A. N. Collins, G. N. Sheldrake and J. Crosby, 1992; John Wiley).

Pharmaceutically acceptable salts of the compounds of formula I may be obtained by treating the free base of the compounds according to formula I with a mineral acid such as hydrochloric acid, phosphoric acid, sulphuric acid, preferably hydrochloric acid, or with an organic acid such as for example ascorbic acid, citric acid, tartaric acid, lactic acid, maleic acid, malonic acid, fumaric acid, glycolic acid, succinic acid, propionic acid, acetic acid, methanesulphonic acid and the like. Pharmaceutically acceptable salts of compounds of formula I wherein $R_1$ is hydrogen, may be obtained by treating the acid or zwitterionic form of those compounds with an organic base or a mineral base, like sodium, potassium or lithium hydroxide.

The invention provides in a further aspect pharmaceutical compositions comprising a spiro[2H-1-benzopyran-2,4'-piperidine] derivative having general formula I, or a pharmaceutically acceptable salt thereof, in admixture with pharmaceutically acceptable auxiliaries.

The pharmaceutical compositions for use according to the invention comprise a spiro[2H-1-benzopyran-2,4'-piperidine] derivative having formula I or a pharmaceutically acceptable salt thereof in admixture with pharmaceutically acceptable auxiliaries, and optionally other therapeutic agents. The term "acceptable" means being compatible with the other ingredients of the composition and not deleterious to the recipients thereof. The compositions can be prepared in accordance with standard techniques such as for example are described in the standard reference, Gennaro et al., Remington's Pharmaceutical Sciences, (18th ed., Mack Publishing Company, 1990, see especially Part 8: Pharmaceutical Preparations and Their Manufacture).

Compositions include e.g. those suitable for oral, sublingual, intranasal, subcutaneous, intravenous, intramuscular, local, or rectal administration, and the like, all in unit dosage forms for administration.

For oral administration, the active ingredient may be presented as discrete units, such as tablets, capsules, powders, granulates, solutions, and suspensions.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

The compounds of the invention may be administered for humans in a dosage of 0.001-50 mg per kg body weight, preferably in a dosage of 0.01-20 mg per kg body weight.

The invention further includes a pharmaceutical composition, as hereinbefore described, in combination with packaging material suitable for said composition, said packaging material including instructions for the use of the composition for the use as hereinbefore described.

The invention is illustrated by the following examples.

General:

All mass spectrometry was carried out on either a PE SCIEX API 150EX or a PE SCIEX API 365 machine. Melting points are uncorrected and were determined using either a Leica Galen III instrument or a Leica VMHB System Kofler.

EXAMPLE 1

1'-Carboxymethyl-7-methoxy-4-phenylspiro[2H-1-benzopyran-2,4°-pineridine]hydrochloride Step A: 7-methoxy-N-methylspiro[2H-1-benzopyran-2,4'-piperidine]-4(3H)-one To a stirred solution of 2-hydroxy-4-methoxyacetophenone (4.08 g, 24.58 mmol) in anhydrous methyl alcohol (60 cm$^3$) under an atmosphere of dry nitrogen was added 1-methyl-4-piperidinone (3 cm$^3$, 24.58 mmol) followed by pyrrolidine (4 cm$^3$, 47.92 mmol) and the solution was heated to reflux. After 7 h, a further portion of 1-methyl-4-piperidinone (0.6 cm$^3$, 4.76 mmol) was added and the mixture was heated to reflux for a further 4.5 h. It was then allowed to cool to room temperature before the volatile fractions were removed under reduced pressure. The resulting oil was treated with dichloromethane (100 cm$^3$), washed with water (5×100 cm$^3$), dried over anhydrous sodium sulfate to afford a dark viscous oil (6.33 g, 24.25 mmol) which partially crystallised on standing over a long period of time.

Step B: 7-methoxy-N-methyl-4-phenyl-spiro[2H-1-benzopyran-2,4'-pipendine]

To a stirred solution of 7-methoxy-N-methylspiro[2H-1-benzopyran-2,4'-piperidine]4(3H)-one (6.19 g, 23.72 mmol), in anhydrous tetrahydrofuran (80 cm$^3$) under an atmosphere of anhydrous nitrogen was added drop-wise a solution of phenylmagnesium bromide in tetrahydrofuran (40 cm$^3$, 1.0 M, 40 mmol) maintaining the reaction temperature below 30° C. When the addition was complete the reaction was stirred at room temperature for 2.5 h at which time the reaction was incomplete but no Grignard reagent was present. A further portion of phenylmagnesium bromide (13.3 Cm$^3$) was carefully added to the reaction and it was allowed to stir overnight. Water (30 cm$^3$) was added followed by saturated aqueous ammonium is chloride solution (30 cm$^3$). The volatiles were removed in vacuo before the resulting material was treated with diethyl ether (100 cm$^3$) and water (100 cm$^3$). The organic layer was separated before the aqueous portion was extracted further with diethyl ether (2×100 cm$^3$). The combined extracts were washed with water (3×100 cm$^3$), dried over sodium sulfate and the ether was removed in vacuo. The residue was triturated with a little diethyl ether and the resulting crystals were isolated by vacuum filtration (4.57 g, 12.15 mmol, 51%). This solid was then taken up into ethyl alcohol (75 cm$^3$) and treated with hydrochloric acid (75 cm$^3$, 2 N) before being heated to reflux for 1.5 h. The solution was concentrated under reduced pressure until a solid began to crystallise. The mixture was then cooled and the solid was isolated by vacuum filtration. This was then treated with a mixture of water (300 cm$^3$), saturated aqueous potassium bicarbonate solution (50 cm$^3$) and diethyl ether (650 cm$^3$) and shaken. The aqueous layer was separated and extracted with diethyl ether (2×100 cm$^3$) before the combined extracts were washed with water (3×250 cm$^3$), dried over sodium sulfate and the volatiles were removed in vacuo to afford the title compound (3.91 g, 12.18 mmol, 51% from ketone).

Step C: 7-methoxy-4-phenylspiro[2H-1-benzopyran-2,4'-piperidine]

To a stirred solution of 7-methoxy-N-methyl-4-phenyl-spiro[2H-1-benzopyran-2,4'-piperidine] (3.76 g, 11.71 mmol) in anhydrous 1,2-dichloropropane (150 cm$^3$) was added potassium carbonate (4.04 g, 29.23 mmol) and the resulting suspension was cooled in an ice-bath before being treated drop-wise with 1-chloroethyl chloroformate (1.58 cm$^3$, 14.64 mmol). The reaction mixture was heated to reflux overnight and a further portion of 1-chloroethyl chloroformate (0.8 cm$^3$, 7.4 mmol) was added before it was heated to reflux for a further 24 h. Upon cooling, the reaction mixture was filtered through cotton wool which was subsequently washed with dichloromethane (50 cm$^3$) and the volatiles were removed in vacuo. The resulting intermediate was treated with methyl alcohol (200 cm$^3$) and the mixture was heated to reflux overnight. Upon cooling, the volatiles were removed in vacuo before the resulting solid was dissolved in a mixture of dichloromethane (150 cm$^3$) and aqueous sodium carbonate solution (5%, 30 cm$^3$). The organic layer was separated, washed with water (2×50 cm$^3$), dried over sodium sulfate and the solvent was removed in vacuo to afford the title compound as a gum (3.93 g).

Step D: ethyl 7-methoxy-4-phenylspiro[2H-1-benzopyran-2,4'piperidine]-1-acetate

To a solution of 7-methoxy-4-phenylspiro[2H-1-benzopyran-2,4'-piperidine] (3.85 g, 12.54 mmol) in anhydrous N,N-dimethylformamide (75 cm$^3$) was added potassium carbonate (4.32 g, 31.30 mmol) followed by ethyl bromoacetate (1.39 cm$^3$, 12.53 mmol) and the mixture was heated to 100° C. under nitrogen for 2 h. The resulting mixture was poured into water (600 cm$^3$) and extracted with ethyl acetate (3×150 cm$^3$). The combined organic extracts were washed with water (3×300 cm$^3$), dried over sodium sulfate and the volatiles were removed in vacuo. This crude product was purified by column chromatography (silica, eluting with dichloromethane-ethyl acetate-9:1 through to 4:1) resulting in the pure ethyl ester (3.51 g, 71%).

Step E: a mixture of ethyl 7-methoxy-4-phenylspiro[2H-1-benzopyran-2,4'-piperidine]1'-acetate (3.38 g, 8.60 mmol), ethyl alcohol (250 cm$^3$) and aqueous lithium hydroxide solution (2 N, 6.44 cm$^3$, 12.88 mmol) was heated to reflux for 3.5 h. Upon cooling, the mixture was treated with hydrochloric acid (5 N, 70 cm$^3$) and some of the ethyl alcohol was removed until precipitation began. The mixture was then cooled to 4° C. until crystallisation was complete. The solid was removed by vacuum filtration to afford the title product as a white solid, m.p. 195-230° C., positive ion ESI (M+H)$^+$ 366.4.

The following compounds were prepared in a similar manner using the appropriate 2'-hydroxyacetophenone derivative of Formula II (Scheme A) and Grignard reagent of formula IV (Scheme B):

EXAMPLE 2

1'-carboxymethyl-4-(4-chlorophenyl)spiro[2H-1-benzopyran-2,4'-piperidine] hydrochloride: m. p. 259-265° C. positive ion ESI (M+H)$^+$ 370.0.

EXAMPLE 3 lithium 4-(4-fluorophenyl)spiro[2H-1-benzopyran-2,4'-piperidine]-1'-acetate:

This lithium salt was prepared analogous to the procedure as described in Example 1 (Step E) except that the hydrolysis of the ethyl ester was carried out using 1.02 mole equivalents of aqueous lithium hydroxide solution (2.0 N) and when the reaction was complete the volatiles were removed in vacuo. m. p. 285-291° C. (decomp.); positive ion ESI (M+H)$^+$ 354.2.

EXAMPLE 4

1'-carboxymethyl-4-(4-methylphenyl)spiro[2H-1-benzopyran-2,4'-piperidine] hydrochloride; m. p. 247-249° C; positive ion ESI (M+H)$^-$352.2.

EXAMPLE 5 lithium 6-fluoro-4-phenylspiro[2H-1-benzopyran-2,4'-piperidine]-1'-acetate: m. p. 293-298° C. (decomp.); negative ion ESI (M+H)$^+$ 354.2.

EXAMPLE 6

1'-carboxymethyl-6-methyl-4-phenylspiro[2H-1-benzopyran-2,4'-piperidine] hydrochloride: m. p. 240-244° C.; positive ion ESI (M+H)$^+$ 350.2.

EXAMPLE 7

1'-carboxymethyl-7-fluoro-4-phenylspiro[2H-1-benzopyran-2,4'-piperidine] hydrochloride: m. p. 237-242° C.; positive ion ESI (M+H)$^+$ 354.2.

EXAMPLE 8

1'-carboxymethyl-4-(4-chloro-3-fluorophenyl)spiro[2H-1-benzopyran-2,4'-piperidine] hydrochloride: m. p. 263-274° C.; positive ion ESI (M+H)$^+$ 388.2.

EXAMPLE 9

1'-carboxymethyl-4-(1-naphthyl)spiro[2H-1-benzopyran-2,4'-piperidine] hydrochloride: m. p. 237-252° C.; positive ion ESI (M+H)$^+$ 385.9.

EXAMPLE 10

1'-carboxymethyl-4-(2-naphthyl)spiro[2H-1-benzopyran-2,4'-piperidine] hydrochloride: m. p. 253-264° C.; positive ion ESI (M+H)$^+$ 386.2.

EXAMPLE 11

1'-carboxymethyl-4-(3-fluoro-4-methoxyphenyl)spiro[2H-1-benzopyran-2,4'-piperidine] hydrochloride: m. p. 252-261° C.; positive ion ESI (M+H)$^+$ 384.2.

EXAMPLE 12

1'-carboxymethyl-4-(4-tert-butylphenyl)spiro[2H-1-benzopyran-2,4'-piperidine] hydrochloride: positive ion ESI (M+H)$^+$ 392.2.

EXAMPLE 13

1'-carboxymethyl-4-(3-fluorophenyl)spiro[2H-1-benzopyran-2,4'-piperidine] hydrochloride: positive ion ESI (M+H)$^+$ 354.4.

EXAMPLE 14

4-(1,3-benzodioxolo)-1'-carboxymethylspiro[2H-1-benzopyran-2,4'-piperidine] hydrochloride: m. p. 260-265° C.; positive ion ESI (M+H)$^+$ 380.4.

EXAMPLE 15

1'-carboxymethyl-4-(3,4-dimethylphenyl)spiro[2H-1-benzopyran-2,4'-piperidine] hydrochloride: m. p. 224-234° C.; positive ion ESI (M−H)$^-$361.9.

EXAMPLE 16

1'-carboxymethyl-4-(3,4-dichlorophenyl)spiro[2H-1-benzopyran-2,4'-piperidine] hydrochloride: positive ion ESI (M+H)$^+$ 404.0.

EXAMPLE 17

1'-carboxymethyl-4-(3,4-dimethoxyphenyl)spiro[2H-1-benzopyran-2,4'-piperidine]hydrochloride: positive ion ESI (M+H)$^+$ 396.2.

EXAMPLE 18

1'-carboxymethyl-4-(3,4,5-trifluorophenyl)spiro[2H-1-benzopyran-2,4'-piperidine] hydrochloride: m. p. 242-250° C.; positive ion ESI (M+H)$^+$ 390.1.

EXAMPLE 19

1'-carboxymethyl-7-fluoro-4-(4-methylphenyl)spiro[2H-1-benzopyran-2,4'-piperidine] hydrochloride: m. p. 153-163° C.; positive ion ESI (M+H)$^+$ 368.0.

EXAMPLE 20

1'-carboxymethyl-4-(4-methoxyphenyl)spiro[2H-1-benzopyran-2,4'-piperidine] hydrochloride: positive ion ESI (M−H)$^-$399.6.

EXAMPLE 21

1'-carboxymethyl-4-(3-chlorophenyl)spiro[2H-1-benzopyran-2,4'-piperidine]hydrochloride; positive ion ESI (M+H)$^+$ 370.2.

EXAMPLE 22

1'-carboxymethyl-4-(3-methoxyphenyl)spiro[2H-1-benzopyran-2,4'-piperidine]hydrochloride: positive ion ESI (M+H)$^+$ 366.4.

EXAMPLE 23

1'-carboxymethyl-4-(3-methylphenyl)spiro[2H-1-benzopyran-2,4'-piperidine]hydrochloride: positive ion ESI (M+H)$^+$ 350.0.

EXAMPLE 24

1'-carboxymethyl-4-[4-(N,N-dimethylamino)phenyl]spiro[2H-1-benzopyran-2,4'-piperidine]hydrochloride.

This compound was prepared according to the methods outlined in Example 1 except that in the final step E the hydrolysis reaction was carried out with 1.5 equivalents of aqueous sodium hydroxide solution (1 M). When the reaction was complete most of the ethyl alcohol was removed and resulting crystals were collected by filtration. This solid was treated with an excess of methanolic hydrogen chloride for 1 h at room temperature. The methyl alcohol was removed in vacuo and the product was treated with 2-propanol-methanol (1:1) and diethyl ether was added drop-wise until the product precipitated. It was isolated by filtration and dried; m. p. 238-250° C.; positive ion ESI (M+H)$^+$ 379.4.

EXAMPLE 25

1'-carboxymethyl-4-(4-ethylphenyl)spiro[2H-1-benzopyran-2,4'-piperidine]hydrochloride; positive ion ESI (M+H)$^+$ 364.4.

EXAMPLE 26

4-(4-biphenyl)-1'-carboxymethylspiro[2H-1-benzopyran-2,4'-piperidine]hydrochloride; positive ion ESI (M+H)$^+$ 412.2.

EXAMPLE 27

1'-carboxymethyl-4-(4-phenoxyphenyl)spiro[2H-1-benzopyran-2,4'-piperidine]hydrochloride; positive ion ESI (M+H)$^+$ 428.2.

EXAMPLE 28

1'-carboxymethyl-4-(3-fluoro-4-methylphenyl)spiro[2H-1-benzopyran-2,4'-piperidine]hydrochloride; positive ion ESI (M+H)$^+$ 368.2.

EXAMPLE 29

1'-carboxymethyl-7-chloro-4-phenylspiro[2H-1-benzopyran-2,4'-piperidine]hydrochloride: positive ion ESI (M+H)$^+$ 370.2.

EXAMPLE 30

1'-carboxymethyl-6-chloro-4-phenylspiro[2H-1-benzopyran-2,4'-piperidine]hydrochloride: positive ion ESI (M+H)$^+$ 370.2.

EXAMPLE 31

1'-carboxymethyl-7-chloro-4-(4-ethylphenyl)spiro[2H-1-benzopyran-2,4'-piperidine]hydrochloride; positive ion ESI (M+H)$^+$ 398.2.

EXAMPLE 32

1'-carboxymethyl-7-chloro-4-(4-propylphenyl)spiro[2H-1-benzopyran-2,4'-piperidine]hydrochloride: positive ion ESI (M+H)$^+$ 412.2.

EXAMPLE 33

1'-carboxymethyl-4-(2,2-difluoro-1,3-benzodioxolo)
spiro[2H-1-benzopyran-2,4'-piperidine]hydrochloride; m. p. 248-250° C.; positive ion ESI (M+H)+
416.2.

EXAMPLE 34

1'-carboxymethyl-4-(2,3,5-trifluorophenyl)spiro[2H-1-benzopyran-2,4'-piperidine]hydrochloride; m. p.
206-210° C.; positive ion ESI (M+H)+ 390.4.

EXAMPLE 35

1'-carboxymethyl-7-chloro-4-(3-fluoro-4-methylphenyl)spiro[2H-1-benzopyran-2,4'-piperidine]hydrochloride; positive ion ESI (M+H)+ 402.3.

EXAMPLE 36

1'-carboxymethyl-4-(3,5-difluoro-4-methoxyphenyl)
spiro[2H-1-benzopyran-2,4'-piperidine]hydrochloride: positive ion ESI (M+H)+ 402.2.

4-Bromo-2,6-difluoroanisole, the starting material for the preparation of the Grignard reagent according to Formula IV (Scheme B), was prepared from 4-bromo-2,6-difluorophenol. To a solution of the phenol (49.0 g, 234 mmol) in anhydrous acetone (980 cm$^3$) was added methyl iodide (29.4 cm$^3$, 468 mmol) followed by potassium carbonate (80.85 g, 585 mmol). The stirred mixture was heated to reflux for 2 h before being allowed to cool. The solid was filtered off and the filtrate was evaporated in vacuo. The residue was taken up into diethyl ether (1000 cm$^3$) and the solution was washed with water (3×300 cm$^3$), dried (Na$_2$SO$_4$) and the ether was removed in vacuo to afford the crude product which was used to prepare the desired is Grignard reagent without further purification (49.4 g, 222 mmol, 95%).

EXAMPLE 37

1'-carboxymethyl-4-(4-dimethylamino-3-fluorophenyl)spiro[2H-1-benzopyran-2,4'-piperidine]hydrochloride: m. p. 231-239° C.; positive ion ESI
(M+H)+ 397.4.

EXAMPLE 38

1'-carboxymethyl-4-(3,5-difluoro-4-dimethylaminophenyl)spiro[2H-1-benzopyran-2,4'-piperidine]
hydrochloride; m. p. 231-242° C.; positive ion ESI
(M+H)+ 415.0.

EXAMPLE 39

4-(4-bromo-3-fluorophenyl)-1'-carboxymethylspiro
[2H-1-benzopyran-2,4'-piperidine]hydrochloride;
positive ion ESI (M+H)+ 432.5.

EXAMPLE 40

1'-carboxymethyl-4-(3-bromo-4-methoxyphenyl)
spiro[2H-1-benzopyran-2,4'-piperidine]hydrochloride; positive ion ESI (M+H)+ 444.1.

EXAMPLE 41

1'-carboxymethyl-4-(3,5-difluorophenyl)spiro[2H-1-benzopyran-2,4'-piperidine]hydrochloride; m. p.
230-264° C.; positive ion ESI (M+H)+ 372.2.

EXAMPLE 42

1'-carboxymethyl-4-(3,5-difluoro-4-ethoxyphenyl)
spiro[2H-1-benzopyran-2,4'-piperidine]hydrochloride:

Step A: 1'-carboxymethyl-4-(3,5-difluoro-4-hydroxyphenyl)spiro[2H-1-benzopyran-2,4'-piperidine]hydrobromide A mixture of the methyl ether (2.35 g) in acetic acid (15 cm$^3$) and 47% hydrobromic acid was stirred at 120° C. for 40 h. The resulting suspension was cooled in an ice-bath before water (30 cm$^3$) was added. The solid was removed by filtration, washed with acetic acid then water before being dried in vacuo.

Step B: ethyl (3,5-difluoro-4-hydroxyphenyl)spiro[2H-1-benzopyran-2,4'-piperidine]-1'-acetate 1'-carboxymethyl-4-(3,5-difluoro-4-hydroxyphenyl)spiro
[2H-1-benzopyran-2,4'-piperidine]hydrobromide (1.7 g; prepared as described in Step A) was suspended in a solution of hydrogen chloride in ethyl alcohol (120 cm$^3$) and the mixture was heated to reflux for 16 h. Upon cooling the volatile materials were removed in vacuo to afford a solid residue which was partitioned between ethyl acetate (100 cm$^3$) and a combination of water (100 cm$^3$) and saturated aqueous potassium bicarbonate (30 cm$^3$). The aqueous layer was extracted into ethyl acetate (2×50 cm$^3$) before the combined extracts were washed with water (2×50 cm$^3$) and dried (Na$_2$SO$_4$). The crude material was then filtered through silica using ethyl acetate as the eluent which was then evaporated to afford the solid product (1.54 g)

Step C: ethyl (3,5-difluoro-4-ethoxyphenyl)spiro[2H-1-benzopyran-2,4-piperidine]-1'-acetate To ethyl (3,5-difluoro-4-hydroxyphenyl)spiro[2H-1-benzopyran-2,4'-piperidine]-1'-acetate (350 mg), cesium carbonate (412 mg) and sodium iodide (13 mg) was added N,N-dimethylformamide (9 cm$^3$) followed by iodoethane (1.7 mole equiv.). The resulting mixtures were heated to 65° C. with stirring for 3 h. Upon cooling, the reaction was diluted with ethyl acetate (90 cm$^3$) then washed with water (5×35 cm$^3$) and dried (Na$_2$SO$_4$). This solution of crude material was then filtered through a pad of silica before the solvent was removed in vacuo to afford the product in a homogeneous state.

Step D: Prepared from ethyl (3,5-difluoro-4-ethoxyphenyl) spiro[2H-1-benzopyran-2,4'-piperidine]-1'-acetate according to the procedure described in Example 1.

1'-carboxymethyl-4-(3,5-difluoro-4-ethoxyphenyl)spiro [2H-1-benzopyran-2,4'-piperidine]hydrochloride: positive ion ESI (M+H)+ 416.5.

Also prepared by this method were:

EXAMPLE 43

1'-carboxymethyl-4-(3,5-difluoro-4-n-propoxyphenyl)spiro[2H-1-benzopyran-2,4'-piperidine]hydrochloride; positive ion ESI (M+H)+ 430.3.

EXAMPLE 44

1'-carboxymethyl-4-(3,5-difluoro-4-n-butoxyphenyl) spiro[2H-1-benzopyran-2,4'-piperidine]hydrochloride; positive ion ESI (M+H)+ 444.4.

EXAMPLE 45

1'-carboxymethyl-4-(4-benzyloxy-3,5-difluorophenyl)spiro[2H-1-benzopyran-2,4'-piperidine]hydrochloride; positive ion ESI (M+H)+ 478.0.

EXAMPLE 46

1'-carboxymethyl-4-(3,5-difluoro-4-iso-pentyloxyphenyl)spiro[2H-1-benzopyran-2,4'-piperidine] hydrochloride; m. p. 211-215° C.; positive ion ESI (M+H)+ 458.5.

EXAMPLE 47

1'-carboxymethyl-4-(4-ethoxy-3-fluorophenyl)spiro [2H-1-benzopyran-2,4'-piperidine]hydrochloride; positive ion ESI (M+H)+ 398.2.

EXAMPLE 48

1'-carboxymethyl-4-(3-fluoro-4-n-propoxyphenyl) spiro[2H-1-benzopyran-2,4'-piperidine]hydrochloride; positive ion ESI (M+H)+ 412.0.

EXAMPLE 49

1'-carboxymethyl-4-(3-fluoro-4-n-butoxyphenyl) spiro[2H-1-benzopyran-2,4'-piperidine]hydrochloride; positive ion ESI (M+H)+ 426.1.

EXAMPLE 50

1'-carboxyimethyl-4-(4-benzyloxy-3-fluorophenyl) spiro[2H-1-benzopyran-2,4'-piperidine]hydrochloride; positive ion ESI (M+H)+ 460.3.

EXAMPLE 51

1'-carboxymethyl-4-(3-fluoro-4-iso-pentyloxyphenyl)spiro[2H-1-benzopyran-2,4'-piperidine]hydrochloride; positive ion ESI (M+H)+ 440.2.

EXAMPLE 52

1'-carboxymethyl-4-(3-fluoro-4-methoxyethoxyphenyl)spiro[2H-1-benzopyran-2,4'-piperidine]hydrochloride; positive ion ESI (M+H)+ 428.2.

EXAMPLE 53

1'-carboxymethyl-4-(3-fluoro-4-iso-butyloxyphenyl) spiro[2H-1-benzopyran-2,4'-piperidine]hydrochloride; positive ion ESI (M+H)+ 425.8.

EXAMPLE 54

1'-carboxymethyl-4-[3-fluoro-4-methoxybenzyloxy) phenyl]spiro[2H-1-benzopyran-2,4'-piperidine]hydrochloride; positive ion ESI (M+H)+ 490.0.

EXAMPLE 55

4-(4-allyloxy-3,5-difluorophenyl)-1'-carboxymethylspiro[2H-1-benzopyran-2,4'-piperidine]hydrochloride:

Step A: N-benzyl-4-(3,5-difluoro-4-allyloxyphenyl)spiro [2H-1-benzopyran-2,4'-piperidine]

Allyl bromide (1.1 mole equiv.) was added dropwise to a mixture of N-benzyl-4-(3,5-difluoro-4-hydroxyphenyl)spiro [2H-1-benzopyran-2,4'-piperidine](750 mg, 1.79 mmol; prepared according to the procedures outlined in Examples 1 and 42), cesium carbonate (1.1 mole equiv.) and anhydrous N,N-dimethylformamide (15 cm³). After stirring for 2 h at room temperature no starting material remained. The reaction mixture was diluted with ethyl acetate (50 cm³) and treated with water (100 cm³) the aqueous layer was separated and re-extracted with ethyl acetate (2×25 cm³). The combined organic extracts were washed with water (4×100 cm³) before being dried (Na₂SO₄) and the volatile materials were removed in vacuo to afford the desired material in high purity (60%).

Step B: 4-(3,5-difluoro-4-allyloxyphenyl)spiro[2H-1-benzopyran-2,4'-piperidine]

The debenzylation was carried out according to Step C in Example 1 with the following exceptions: dichloromethane was used as the solvent (which was not specifically dried) and the reactions were not carried out under an inert atmosphere. In some examples the breakdown of the intermediate carbamate was ineffective when heated to reflux in the presence of methyl alcohol. In such cases the addition of an excess of 10 N aqueous potassium hydroxide with heating to reflux overnight was required.

From this point on the amine was converted through to the final compound according to the procedures described in Example 1: m. p. 221-225° C.; positive ion ESI (M+H)+ 428.2.

EXAMPLE 56

1'-carboxymethyl-4-(3,5-difluoro-4-iso-propyloxyphenyl)spiro[2H-1-benzopyran-2,4'-piperidine] hydrochloride; m. p. 241-243° C.; positive ion ESI $(M+H)^+$ 430.3.

EXAMPLE 57

1'-carboxymethyl-4-(3,5-difluoro-4-propargyloxyphenyl)spiro[2H-1-benzopyran-2,4'-piperidine] hydrochloride; m. p. 211-217° C.; positive ion ESI $(M+H)^+$ 426.1.

EXAMPLE 58

1'-carboxymethyl-4-(3,5-difluoro-4-cyclopropylmethoxyphenyl)spiro[2H-1-benzopyran-2,4'-piperidine]hydrochloride; m. p. 225-231° C.; positive ion ESI $(M+H)^+$ 442.0.

EXAMPLE 59

1'-carboxymethyl-4-(3,5-difluoro-4-trifluoroethoxyphenyl)spiro[2H-1-benzopyran-2,4'-piperidine] hydrochloride; m. p. 244-251° C.; positive ion ESI $(M+H)^+$ 470.2.

EXAMPLE 60

1'-carboxymethyl-4-(3-fluoro-4-iso-propyloxyphenyl)spiro[2H-1-benzopyran-2,4'-piperidine]hydrochloride; m. p. >260° C.; positive ion ESI $(M+H)^+$ 412.4.

EXAMPLE 61

1'-carboxymethyl-4-(3-fluoro-4-trifluoroethoxyphenyl)spiro[2H-1-benzopyran-2,4'-piperidine]hydrochloride; m. p. 230-235° C.; positive ion ESI $(M+H)^+$ 452.2.

EXAMPLE 62

1'-carboxymethyl-4-(3-fluoro-4-phenoxyphenyl)spiro[2H-1-benzopyran-2,4'-piperidine]hydrochloride; m. p. 160-180° C.; positive ion ESI $(M+H)^+$ 446.0.

EXAMPLE 63

Lithium 4-phenylspiro[2H-1-benzopyran-2,4'-piperidine]-1'-acetate; m. p. 280-281° C.; positive ion ESI $(M+H)^+$ 336.2.

EXAMPLE 64

Lithium 4-(4-trifluoromethylphenyl)spiro[2H-1-benzopyran-2,4'-piperidine]-1'-acetate: positive ion ESI $(M-Li+2H)^+$ 404.4.

EXAMPLE 65

Ethyl 4-(4-ethylphenyl)spiro[2H-1-benzopyran-2,4'-piperidine]-1'-acetate; m. p. 119-121° C.; positive ion ESI $(M+H)^+$ 392.3.

EXAMPLE 66

Phenyl 4-(4-ethylphenyl)spiro[2H-1-benzopyran-2,4'-piperidine]-1'-acetate; m. p. 104-105° C.; positive ion ESI $(M+H)^+$ 440.3.

EXAMPLE 67

1'-carboxymethyl-4-(4-iso-pentyloxyphenyl)spiro[2H-1-benzopyran-2,4'-piperidine]hydrochloride; positive ion ESI $(M+H)^+$ 422.0.

EXAMPLE 68

Sodium [4-(2-pyridinomethyloxy)phenyl]spiro[2H-1-benzopyran-2,4'-piperidine]-1'-acetate; prepared according to Example 42 using 2-picolylchloride hydrochloride. The final hydrolysis was carried out according to Example 1 except that sodium hydroxide was used; positive ion ESI $(M+H)^+$ 443.4.

EXAMPLE 69

1'-carboxymethyl-4-[4-(4-methylphenylsulfonyloxy)phenyl]spiro[2H-1-benzopyran-2,4'piperidine]hydrochloride.

Step A: 1'-carboxymethyl-4-[4-methylphenyslsulfonyloxy)phenyl]spiro[2H-1-benzopyran-2,4'piperidine]ethyl Ester.

To a mixture of ethyl (4-hydroxyphenyl)spiro[2H-1-benzopyran-2,4'-piperidine]-1'-acetate (182 mg, 0.5 mmol; prepared according to Example 42) dichloromethane (13 cm³) and pyridine (158 mg, 2.0 cm³) being stirred at -5° C., was carefully added a solution of p-toluenesulphonyl chloride (288 mg 1.5 mmol) in dichloromethane (13 cm³). The reaction was then allowed to rise to ambient temperature, stirred for a further 2 h and then the solution left to stand overnight. Water (7 cm³) was added to the mixture and after stirring for 10 min the solvent was evaporated to give the product as a gum which solidified on standing. This was broken up with a spatula, filtered off and washed with water (20 cm³). The cake was sucked almost dry and then finally dried in vacuo at 65° C. to give the product (300 mg), $(M+H)^+$ =534.2 m/z.

This ester was hydrolysed according to the procedure described in Example 1 except that the hydrolysis was carried out in n-butanol: positive ion ESI (M+H)+ 506.2.

EXAMPLE 70

1'-carboxymethyl-8-fluoro-4-phenylspiro[2H-1-benzopyran-2,4'-piperidine]hydrochloride.

When the required starting 2'-hydroxyacetophenone was not commercially available it could be prepared as described below:

Step A: (2-fluorophenyl) Acetate

Acetic anhydride (81 cm³, 856 mmol) was added dropwise to a stirred mixture of 2-fluorophenol (60.0 g, 535 mmol) and aqueous sodium hydroxide (4 N, 214 cm³, 856 mmol) at 0° C. After the reaction had been stirred for 30 min the aqueous layer was separated from the organic portion and washed with dichloromethane (150 cm³). The combined organic extracts were washed with aqueous sodium hydroxide solution (4 N, 150 cm³) and then brine (100 cm³). The organic phase was dried (Na₂SO₄) and the solvent was evaporated in vacuo to afford the title compound (84.9 g, >100%).

Step B: 2'-hydroxy-3'-fluoro Acetophenone

Finely powdered aluminium trichloride (32.0 g, 239 mmol) was added to (2-fluorophenyl) acetate (23.0 g, 149 mmol) and the mixture was heated to 180° C. for 1 h. Upon cooling to room temperature, the reaction mixture was carefully poured onto ice/water and the product was extracted into dichloromethane (150 cm$^3$). The organic layer was separated, washed with brine (150 cm$^3$), dried (Na$_2$SO$_4$) and the solvent was removed in vacuo. The crude reaction mixture was purified by column chromatography (silca gel, dichloromethane-methyl alcohol 99:1) to afford the title compound (3.1 g, 14%).

From this point on the acetophenone was converted through to the final compound according to the procedures described in Example 1: m. p. 180-182° C.; positive ion ESI (M+H)$^+$ 354.0.

Also prepared according to this route was:

EXAMPLE 71

1'-carboxymethyl-7-chloro-6-fluoro-4-phenylspiro [2H-1-benzopyran-2,4'-piperidine]hydrochloride; m. p. 275-293° C.; positive ion ESI (M+H)$^+$ 387.7.

EXAMPLE 72

1'-carboxymethyl-5-fluoro-4-phenylspiro[2H-1-benzopyran-2,4'-piperidine]hydrochloride.

The required starting 2'-hydroxyacetophenone was not commercially available and therefore had to be prepared as described below:

Step A: 2'-fluoro-6'-methoxyacetophenone

A mixture of 2-fluoro-6-methoxybenzonitrile (15.94 g, 105.5 mmol) and a solution of methyl magnesium iodide in diethyl ether (3 M, 46.0 cm$^3$, 137 mmol) was heated to 100° C. for 18 h. Upon cooling to room temperature, aqueous hydrochloric acid (3 M, 94 cm$^3$) was added and the mixture was heated to reflux to for 4 h. When the reaction had cooled to room temperature the organic layer was separated and the aqueous phase was extracted with ethyl acetate (100 cm$^3$). The combined organic extracts were washed with brine (100 cm$^3$) before being dried (Na$_2$SO$_4$). The solvent was removed in vacuo to afford the title compound as an oil (117.7 g, 100%).

Step B: 2'-fluoro-6'-hydoxyacetophenone

A solution of boron tribromide in dichloromethane (69.0 cm$^3$, 69.6 mmol) was added dropwise over a period of 25 min to a solution of 2'-fluoro-6'-methoxyacetophenone (17.72 g, 105.5 mmol) in dichloromethane (150 cm$^3$) at −78° C. After allowing the reaction to warm to 0° C. it was quenched with water (100 cm$^3$) and the product was extracted into dichloromethane (100 cm$^3$). The organic solution was washed with water (100 cm$^3$), brine (150 cm$^3$) and then dried (Na$_2$SO$_4$). Evaporation of the solvent in vacuo afforded the crude product which was taken forward without purification.

From this point on the acetophenone was converted through to the final compound according to the procedures described in Example 1: m. p. 252-254° C.; positive ion ESI (M+H)$^+$ 354.2.

EXAMPLE 73

1'-carboxymethyl-4-[4-(2-ethoxymorpholino)phenyl] spiro[2H-1-benzopyran-2,4'-piperidine]hydrochloride.

Prepared according to the methods described in Example 42 by alkylating the appropriate phenol with 4-(2-chloroethyl)morpholine hydrochloride; positive ion ESI (M+2H)$^+$ 465.2.

EXAMPLE 74

1'''-carboxymethyl-6-hydroxy-4-phenylspiro[2H-1-benzopyran-2,4'-piperidine]hydrochloride.

Prepared according to the methods described in Examples 1 and 42; positive ion ESI (M+H)$^+$ 352.2.

EXAMPLE 75

1'-carboxymethyl-7-methylthio-4-phenylspiro[2H-1-benzopyran-2,4'-piperidine]hydrochloride.

Step A: 7-fluoro-N-methylspiro[2H-1-benzopyran-2,4'-piperidine]-4(3H)-one

A stirred solution of 4'-fluoro-2'-hydroxyacetophenone (15.97 g), 1-methyl-4-piperidone (12.74 cm$^3$) and pyrrolidine (4.325 cm$^3$) in methyl alcohol (250 cm$^3$) was heated to reflux under nitrogen. After 0.5 h, further pyrrolidine (4.33 cm$^3$) was added and, after another 0.5 h, the solution was allowed to cool. The reaction mixture was then evaporated under reduced pressure to give an oil, which was dissolved in dichloromethane (400 cm$^3$). This solution was washed with water (3×400 cm$^3$), dried (Na$_2$SO$_4$) and evaporated to give an oil (25.7 g). Flash chromatography on silica (eluting with dichloromethane-methyl alcohol-33% aqueous ammonia=380:20:1) gave the purified product as an oil (14.41 g).

Step B: 7-methylthio-N-methylspiro[2H-1-benzopyran-2,4'-piperidine]-4(3H)-one

To a stirred solution of 7-fluoro-N-methylspiro[2H-1-benzopyran-2,4'-piperidine]-4(3H)-one (4.54 g) in dimethylformamide (20 cm$^3$) under nitrogen was added sodium thiomethoxide (1.40 g). The mixture was stirred at room temperature for 1.25 h, at 60° C. for 4.5 h and then was allowed to cool and to stand overnight at room temperature. It was stirred and heated at 130° C. for 2.5 h then was allowed to cool and to stand overnight at room temperature before being poured into stirred water (140 cm$^3$). The solid product was filtered off, washed with water and dissolved in dichloromethane. The solution was dried (Na$_2$SO$_4$) and evaporated to give the product as a gum (4.44 g).

From this point on the 7-methylthio-N-methylspiro[2H-1-benzopyran-2,4'-piperidine]-4(3H)-one was converted through to the final compound according to the procedure described in Example 1 with the following exception: in the work-up of the demethylation step the required secondary amine was converted unexpectedly into a less polar compound which was treated with aqueous potassium hydroxide (10 N) in methyl alcohol at reflux to regenerate the required amine; (M+H)$^+$ =382.0.

EXAMPLE 76

1'-carboxymethyl-4-(4-trifluoromethoxyphenyl)spiro
[2H-1-benzopyran-2,4'-piperidine]hydrochloride.

Step A: Trifluromethanesulfonic Acid-4-[1'-phenylmethyl-spiro(2H-1-benzopyran-2,4°-piperidine)]ester.

To a cooled stirred solution (-78° C.) of the N-benzylspiro [2H-1-benzopyran-2,4'-piperidine]4(3H)-one (1.54 g, 5 mmol; prepared as in Example 1) in dry tetrahydrofuran (40 cm$^3$) was added lithium hexamethyidisilazide (1 M solution in hexane, 7.5 cm$^3$, 7.5 mmol) dropwise over a period of ca. 5 min. After stirring at that temperature for 1 h the N-phenyl-trifluoromethane sulfonamide (2.68 g, 7.5 mmol) was added in one portion and the resulting reaction mixture was left to stir and warm up slowly overnight. The reaction was quenched with water (10 cm$^3$) and extracted into ethyl acetate (2×50 cm$^3$). The organic portion was washed with saturated aqueous ammonium chloride (50 cm$^3$), saturated aqueous sodium chloride (50 cm$^3$) and water (50 cm$^3$) before being dried (Na$_2$SO$_4$) and concentrated. The product was purified by column chromatography on silica (3:1 heptane-ethyl acetate) to afford the desired material (1.75 g, 80%) which was either used immediately or stored under an inert atmosphere at −20° C.

Step B: N-benzyl-4-(4-trifluoromethoxyphenyl)spiro[2H-1-benzopyran-2,4'-piperidine]-4(3H)-one A mixture of {N-benzylspiro[2H-1-benzopyran-2,4'-piperidine]}4-(phenyl-4-trifluoromethylsulfonate) (1.69 g, 3.86 mmol), 4-trifluoromethoxybenzene boronic acid (1.25 equiv.), dimethoxyethane (40 cm$^3$), lithium chloride (2.5 equiv.), tetrakis(triphenylphosphine)palladium (0) (2.5 mol %) and aqueous 2 N sodium carbonate solution (2 equiv.) was heated to reflux for 12 h. Upon cooling, the mixture was treated with water (75 cm$^3$) and ethyl acetate (75 cm$^3$). After shaking the organic layer was separated and washed with water (2×100 cm$^3$), dried (Na$_2$SO$_4$) and the solvent was removed to yield the desired product (96%) which was used in the next step without further purification.

From this point on the N-benzyl-4-(4-trifluoromethoxyphenyl)spiro[2H-1-benzopyran-2,4'-piperidine]-4(3H)-one was converted through to the final compound according to the procedure described in Example 1; m.p. 233-237° C.; (M+H)$^+$ =420.2.

EXAMPLE 77

1'-carboxymethyl-4-(4-methylthiophenyl)spiro[2H-1-benzopyran-2,4'-piperidine]hydrochloride. Prepared according to the methods described in Examples and 76; positive ion ESI (M+H)$^+$ 352.2.

EXAMPLE 78

1'-carboxymethyl-4-[4-(N-methyl-N-methylsulfonamido)phenyl]-spiro[2H-1-benzopyran-2,4'-piperidine]hydrochloride.

Step A: ethyl 4-(4-hydroxyphenyl)spiro[2H-1-benzopyran-2, 4'-piperidine]-1'-acetate To a mixture of 1'-carboxymethyl-4-(4-hydroxyphenyl) spiro[2H-1-benzopyran-2,4'-piperidine]-1'-acetate (432 mg, 1 mmol., prepared according to Example 42), sodium hydrogen carbonate (176 mg, 2.1 mmol) in dry N,N-dimethylformamide (25 cm$^3$) was added ethyl iodide (0.088 cm$^3$, 1.1 mmol) and the mixture was heated to 0.80° C. for 2 h. Upon cooling, it was diluted with ethyl acetate (100 cm$^3$) and washed with water (5×100 cm$^3$). The organic solution was then dried over sodium sulfate before the solvent was removed in vacuo. The crude material was then passed through a short pad of silica first with dichloromethane (which was discarded) and then with ethyl acetate. The solvent was removed to afford the desired product (194 mg, 51%).

Step B: Trifluoromethanesulfonic Acid-{1'-carboxymethyl-4-phenylspiro[2H-1-benzopyran-2,4'-piperidine]ethyl Ester}

To a cooled (−20° C.), stirred suspension of ethyl 4-(4-hydroxyphenyl)spiro[2H-1-benzopyran-2,4'-piperidine]-1'-acetate (158 mg, 4.16×10$^{-4}$ mol) in anhydrous dichloromethane (10 cm$^3$) under an inert atmosphere was added triethylamine (0.065 cm$^3$, 4.6×10$^{-4}$ mol). After 10 min a solution of trifluoromethanesulfonic anhydride (0.077 cm$^3$, 4.6×10$^{-4}$ mol) in dichloromethane (7.7 cm$^3$) was added dropwise over a period of ca. 5 min. During the next ca. 20 min the solid material disappeared. However, analysis by thin layer chromatography revealed that the reaction was incomplete so a further portion of the trifluoromethanesulfonic anhydride was added (0.25 equiv.). After a further ca. 20 min, the reaction mixture was diluted with ethyl acetate (60 cm$^3$) and then washed with water (3×60 cm$^3$) before being dried (Na$_2$SO$_4$) and the solvent removed in vacuo. The crude product was purified by column chromatography on silica (3:1 dichloromethane-ethyl acetate) to afford the desired material (154 mg, 75%).

St p C: 4-[4-(diphenylimino)phenyl]spiro[2H-1-benzopyran-2,4'-piperidine]-1-acetic Acid Ethyl Ester.

The title compound was prepared by a modification of the procedure of Buchwald et al., Tetrahedron Letters, 1997, 38, 6367.

To a solution of trifluoromethanesulfonic acid-{1'-carboxymethyl-4-phenylspiro[2H-1-benzopyran-2,4'-piperidine]ethyl ester} (421 mg, 8.43×10$^{-4}$ mol) in dry tetrahydrofuran (25 cm$^3$), being stirred at room temperature under an atmosphere of dry nitrogen, was added benzophenone imine (1.2 equiv., 0.283 cm$^3$). This was followed by the addition of palladium acetate (1.25 mol %), (R)-(+)2,2'-bis(diphenylphosphino)-1,1'-binaphthyl (3.75 mol %) and cesium carbonate (1.40 equiv., 385 mg). The mixture was heated to reflux for 24 h before being allowed to cool to room temperature. It was then diluted with (non-dry) diethyl ether (250 cm$^3$), filtered through a pad of filter aid and then the volatiles were removed in vacuo. The residue was purified by column chromatography on silica (1:1 heptane-ethyl acetate) to afford the desired material (547 mg; contaminated with benzophenone imine).

Step D: ethyl 4-(4-aminophenyl)spiro[2H-1-benzopyran-2, 4°-piperidine]-1'-acetate The title compound was prepared according to the procedure of Buchwald et al., *Tetrahedron Letters*, 1997, 38, 6367.

To a stirred solution of ethyl 4-(4-benzophenoneiminophenyl)spiro[2H-1-benzopyran-2,4'-piperidine]-1'-acetate (542 mg, 1 mmol) in methyl alcohol (25 cm$^3$) was added sodium acetate (198 mg, 2.4 mmol) followed by hydroxylamine hydrochloride (125 mg, 1.8 equiv.) and the reaction was allowed to stir at room temperature for 30 min. The methyl alcohol was removed in vacuo before the residue was partitioned between dichloromethane (25 cm$^3$) and aqueous sodium hydroxide solution (0.1 M, 25 cm$^3$). The organic layer was isolated and the volatiles were removed in vacuo before the product was purified by column chromatography (silica, ethyl acetate) (220 mg, 69% from triflate).

Step E: ethyl 4-(methyl 4-phenylsulfonamide)spiro[2H-1-benzopyran-2,4'-piperidine]-1'-acetate The title compound was prepared according to the procedure of R. J. Sundberg et al., *Journal of Organic chemistry*, 1984, 49, 249.

A flask containing a mixture of ethyl 4-(4-aminophenyl) spiro[2H-1-benzopyran-2,4'-piperidine]-1'-acetate (214 mg, 0.566 mmol), pyridine (3 equiv., 0.137 cm$^3$) and anhydrous dichloromethane (10 cm$^3$) was allowed to stir in an ice/methyl alcohol bath. After 10 min at this temperature a solution of methanesulfonyl chloride (1.5 equiv., 0.066 cm$^3$) in dry dichloromethane (0.66 cm$^3$) was added dropwise over a period of ca. 5 min. After stirring for 2 h, the reaction mixture was poured onto a saturated aqueous solution of potassium hydrogen carbonate (10 cm$^3$). The organic layer was washed with water (3×50 cm$^3$) and the solvent removed in vacuo. Toluene (30 cm$^3$) was added and then removed in vacuo (this was repeated until the smell of pyridine ceased) and then methyl alcohol was added (30 cm$^3$) and removed. The remaining material was homogeneous (234 mg, 91%).

Step F: ethyl 4-(methyl 4-phenyl-N-methylsulfonamide) spiro[2H-1-benzopyran-2,4'-piperidine]-1'-acetate To a solution of ethyl 4-(methyl 4-phenylsulfonamide) spiro[2H-1-benzopyran-2,4'-piperidine]-1'-acetate (108 mg, 0.236 mmol) in methyl alcohol (10 cm$^3$) was added a solution of trimethylsilyl diazomethane (2 M in hexanes, 5 cm$^3$) in the absence of stirring. Immediately upon the addition evolution of nitrogen was observed. After standing for 1 h at room temperature the volatiles were removed in vacuo before the residue was purified by column chromatography (silica, ethyl acetate) to afford the homogeneous product (74 mg, 67%).

1'-carboxymethyl 4-(N-methyl 4-phenyl-N-methyl-sulfonamide)spiro[2H-1-benzopyran-2,4'-piperidine] hydrochloride From this point on the synthesis proceeded according to the method described in Example 1; positive ion ESI (M+H)$^+$ =443.2.

EXAMPLE 80

1'-carboxymethyl-4-(4-amino-3,5-difluorophenyl) spiro[2H-1-benzopyran-2,4'-piperidine]dihydrochloride.

(4-Bromo-2,5-difluorophenyl)-2,5-dimethylpyrrole was prepared according to the procedure of Bruekelmann et al., *J. Chem. Soc., Perkin Trans.* 1, 1984, 2801.

This material was converted to the corresponding Grignard reagent and allowed to react with N-methylspiro[2H-1-benzopyran-2,4'-piperidine]-4(3H)-one according to Example 1 except that an unresolved mixture of the pyrrole and the deprotected aniline was obtained. This mixture was N-dealkylated as described in Example 1 (along with concomitant deprotection of the aniline function) to afford 4-(4-amino-3,5-difluorophenyl)spiro[2H-1-benzopyran-2,4'-piperidine]. The resulting amine was then alkylated with ethyl bromoacetate and the resulting ester hydrolysed according to Example 1; positive ion ESI (M+H)$^+$ 387.1.

EXAMPLE 81

1'-carboxymethyl-3,4-dihydro-4-(4-methylphenyl) spiro[2H-1-benzopyran-2,4'-piperidine]hydrochloride.

Step A: ethyl 3,4-dihydro-4-(4-methylphenyl)spiro[2H-1-benzopyran-2,4'-piperidine]-1'-acetate.

To a solution of ethyl 4-(4-methylphenyl)spiro[2H-1-benzopyran-2,4'-piperidine]-1'-acetate (730 mg, 0.194 mmol) in ethyl alcohol (125 cm$^3$) was added 10% palladium on carbon. This mixture was heated to 40° C. for 7 h under an atmosphere of hydrogen (4 bar) and then it was filtered whilst still warm and the filter cake was washed with hot ethyl alcohol (3×50 cm$^3$). The solvent was removed in vacuo and the resulting compound was recrystallised from ethyl alcohol (67%). This ester was hydrolysed according to the procedure in Example 1; m.p. 247-249° C.; (M+H)$^+$ =352.2.

Also prepared by this method was:

EXAMPLE 82

Lithium 3,4-dihydro-4-(4-fluorophenyl)spiro[2H-1-benzopyran-2,4'-piperidine]-1'-acetate: m. p. 274-278° C. (decomp.); negative ion ESI (M−Li)$^-$ 354.4.0.

EXAMPLE 83

Method for Determination of Glycine Uptake in CHO Cells Heterologously Expressing the Human GlyT-1b Transporter.

A: Cloning: cDNA was generated by PCR according to the method described by Kim, K.-M. et al. Mol. Pharmacol. 1994, 45, 608-617. Sequence was verified by dideoxy sequencing using the ALF DNA sequencer™ (Pharmacia) and cloned into the expression construct pcDNA3 (Invitrogen).

B: Transfection: Transfection of hGlyT-1b into CHO cells was performed using a standard calcium phosphate technique as described by Sambrook, J. et al. (1989) in *Molecular Cloning: A Laboratory Manual*, Cold Spring Harbor Laboratory, Cold Spring Harbor, N.Y.

C: Selection: Stably transfected cells were selected for 1 week in growth medium containing 1 mg·cm$^3$ Geneticin. Individual clones were picked for further analysis and positives passaged routinely as described below.

D: Culture conditions: Cells stably expressing the hGlyT-1b gene were cultured at 37° C. in a 5% CO$_2$ atmosphere in DMEM—NUT.MIX. F12 with Glutamax-1 (Gibco) containing Geneticin (0.5 mg·cm$^{-3}$, Gibco) and supplemented with 10% Fetalclone II (Hyclone). Maintenance culture was carried out in standard 80 cm$^2$ ventilated flasks (2×10$^{-6}$ m filter, Nunc) and cells were subcultured by trypsinisation (Sigma) when confluent.

E: Assay Procedure: Cells for uptake studies were plated in 96 well plates (17,000 cells per well) in the absence of Geneticin and cultured for 48 h before use. To measure glycine transport, cells were washed twice with Hanks' balanced salt solution (HBSS) pre-warmed to 37° C. and excess fluid removed before addition of test compounds dissolved in 0.200 cm$^3$ HBSS. Plates were incubated at 37° C. for 5 minutes before addition of [$^3$H]glycine (0.050 cm$^3$, 150×10$^{-6}$ M, 248 Bq.n- mol$^{-1}$, NEN) and incubation continued for a further 10 minutes. Uptake was terminated by washing cells with ice-cold HBSS before removal of excess fluid and addition of 02.00 cm$^3$ scintillation cocktail to each well. Plates were sealed with adhesive film, shaken to ensure samples were homogenous before scintillation counting in a plate counter.

F: Data Analysis: Data were analysed using standard curve fitting procedures to produce a pIC$_{50}$ value for active compounds (where pIC$_{50}$ is the negative logarithm of the concentration of test compound causing 50% inhibition of uptake).

G: Results: The compounds of the invention selectively inhibit the glycine transport by the human GlyT-1b transporter as compared to the human GlyT-2 transporter (the modular cloning and functional expression of the human GlyT-2 transporter is described by Morrow, J. A. et al. FEBS letters 1998, 439, 334-340. The pIC$_{50}$ values for a number of compounds of the invention are given in Table I.

TABLE I

| | Inhibition of glycine transport by hGlyT-1 | |
|---|---|---|
| EXAMPLE | COMPOUND | pIC$_{50}$ |
| 2 | 1'-carboxymethyl-4-(4-chlorophenl)spiro[2H-1-benzopyran-2,4'-piperidine] hydrochloride | 6.0 |
| 4 | 1'-carboxymethyl-4-(4-methylphenyl) spiro[2H-1-benzopyran-2,4'-piperidine] hydrochloride | 6.3 |
| 8 | 1'-carboxymethyl-4-(4-chloro-3-fluorophenyl) spiro[2H-1-benzopyran-2,4'-piperidine] hydrochloride | 6.3 |
| 10 | 1'-carboxymethyl-4-(2-naphthyl) spiro[2H-1-benzopyran-2,4'-piperidine] hydrochloride | 6.2 |
| 11 | 1'-carboxymethy-4-(3-fluoro-4-methoxyphenyl) spiro[2H-1-benzopyran-2,4'-piperidine] hydrochloride | 6.2 |
| 12 | 1'-carboxymethy-4-(4-tert-butylphenyl) spiro[2H-1-benzopyran-2,4'-piperidine] hydrochloride | 6.4 |
| 14 | 4-(1,3-benzodioxolo)-1'-carboxymethylspiro[2H-1-benzopyran-2,4'-piperidine] hydrochloride | 6.1 |
| 24 | 1'-carboxymethyl-4-[4-(N,N-dimethylamino)phenyl] spiro[2H-1-benzopyran-2,4'-piperidine] hydrochloride | 6.2 |
| 28 | 1'-carboxymethyl-4-(3-fluoro-4-methylphenyl) spiro[2H-1-benzopyran-2,4'-piperidine] hydrochloride | 6.5 |
| 33 | 1'-carboxymethyl-4-(2,2-difluoro-1,3-benzodioxolo)spiro[2H-1-benzopyran-2,4'-piperidine] hydrochloride | 6.2 |
| 35 | 1'-carboxymethyl-7-chloro-4-(3-fluoro-4-methylphenyl)spiro[2H-1-benzopyran-2,4'-piperidine] hydrochloride | 6.3 |
| 36 | 1'-carboxymethyl-4-(3,5-difluoro-4-methoxyphenyl) spiro[2H-1-benzopyran-2,4'-piperidine] hydrochloride | 6.4 |
| 37 | 1'-carboxymethyl-4-(4-dimethylamino-3-fluorophenyl)spiro[2H-1-benzopyran-2,4'-piperidine] hydrochloride | 6.4 |
| 38 | 1'-carboxymethyl-4-(3,5-difluoro-4-dimethylaminophenyl)spiro[2H-1-benzopyran-2,4'-piperidine] hydrochloride | 6.6 |
| 39 | 4-(4-bromo-3-fluorophenyl)-1'-carboxymethylspiro[2H-1-benzopyran-2,4'-piperidine] hydrochloride | 6.1 |
| 48 | 1'-carboxymethyl-4-(3-fluoro-4-n-propoxyphenyl)spiro[2H-1-benzopyran-2,4'-piperidine] hydrochloride | 6.3 |
| 49 | 1'-carboxymethyl-4-(3-fluoro-4-n-butoxyphenyl)spiro[2H-1-benzopyran-2,4'-piperidine] hydrochloride | 6.1 |
| 55 | 4-(4-allyloxy-3,5-difluorophenyl)-1'-carboxymethylspiro[2H-1-benzopyran-2,4'-piperidine] hydrochloride | 6.6 |
| 57 | 1'-carboxymethyl-4-(3,5-difluoro-4-propargyloxyphenyl)spiro[2H-1-benzopyran-2,4'-piperidine] hydrochloride | 6.6 |
| 59 | 1'-carboxymethyl-4-(3,5-difluoro-4-trifluoroethoxyphenyl)spiro[2H-1-benzopyran-2,4'-piperidine] hydrochloride | 6.6 |

We claim:

1. A spiro[2H-1-benzopyran-2,4'-piperidine] derivative having formula I:

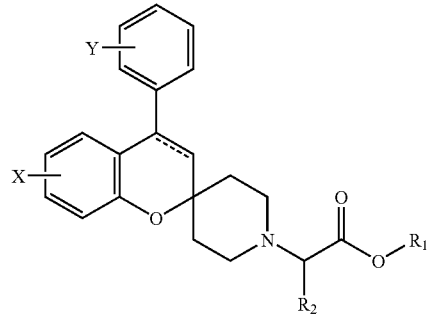

Formula I wherein the dotted line represents an optional bond;

Y represents 1-2 substituents independently selected from hydrogen, halogen, (C$_{1-6}$)alkyl optionally substituted with one or more halogens, (C$_{1-6}$)alkyloxy optionally substituted with one or more halogens, (C$_{2-6}$)alkenyloxy, (C$_{2-6}$)alkynyloxy, pyridinylmethyloxy, SR$_3$, NR$_3$R$_4$, OSO$_2$R$_5$, and NR$_3$SO$_2$R$_4$; or 2 substituents Y may together form O—(CH$_2$)$_n$—O or O—(CF$_2$)$_n$—O, where n is 1 or 2;

X represents 1-3 substituents independently selected from hydrogen, halogen, hydroxy, (C$_{1-4}$)alkyloxy, SR$_3$, NR$_3$SO$_2$R$_4$ and (C$_{1-4}$)alkyl, optionally substituted with halogen;

R$_1$ is hydrogen, (C$_{1-4}$)alkyl or (C$_{6-12}$)aryl;

R$_2$, R$_3$ and R$_4$ are independently hydrogen or (C$_{1-4}$) alkyl;

R$_5$ is (C$_{1-4}$)alkyl (optionally substituted with one or more halogens) or (C$_{6-12}$)aryl (optionally substituted with (C$_{1-4}$)alkyl); or a pharmaceutically acceptable salt thereof, wherein at least one of Y represents 1 substituent selected from pyridinylmethyloxy; or at least 2 substituents Y together form O—(CH$_2$)$_n$—O or O—(CF$_2$)$_n$—O, where n is 1 or 2.

2. The spiro[2H-1-benzopyran-2,4'-piperidine] derivative according to claim 1, wherein the dotted line represents a bond.

3. The spiro[2H-1-benzopyran-2,4'-piperidine] of claim 1, wherein R$_1$ and R$_2$ are hydrogen.

4. The spiro[2H-1-benzopyran-2,4'-piperidine] of claim 1, wherein Y represents is pyridinylmethyloxy.

5. A pharmaceutical composition, comprising: a spiro[2H-1-benzopyran-2,4'-piperidine] according to claim 1, or a pharmaceutically acceptable salt thereof, in admixture with pharmaceutically acceptable auxiliaries.

* * * * *